United States Patent [19]

Austin et al.

[11] 4,210,606

[45] Jul. 1, 1980

[54] DECOMPOSITION OF CUMENE HYDROPEROXIDE WITH A HALOGEN-SUBSTITUTED THIOPHENOL CATALYST

[75] Inventors: Richard G. Austin, Churchill; Wayne R. Pretzer; Thaddeus P. Kobylinski, both of Gibsonia, all of Pa.

[73] Assignee: Gulf Research and Development Company, Pittsburgh, Pa.

[21] Appl. No.: 48,743

[22] Filed: Jun. 15, 1979

[51] Int. Cl.$^2$ ................ C07C 45/00; C07C 37/08
[52] U.S. Cl. ............................ 568/385; 568/798; 568/715; 585/437; 568/311

[58] Field of Search ............ 260/593 A, 592, 669 QZ; 568/798, 715

[56] References Cited

U.S. PATENT DOCUMENTS

| 2,663,735 | 12/1953 | Filar et al. | 568/798 |
| 3,928,477 | 12/1975 | Field et al. | 260/593 A |
| 4,075,250 | 2/1978 | Field et al. | 260/593 A |

*Primary Examiner*—Norman Morgenstern
*Assistant Examiner*—James H. Reamer

[57] ABSTRACT

Cumene hydroperoxide is decomposed to phenol and acetone using a halogen-substituted thiophenol as the catalyst.

8 Claims, No Drawings

DECOMPOSITION OF CUMENE HYDROPEROXIDE WITH A HALOGEN-SUBSTITUTED THIOPHENOL CATALYST

FIELD OF THE INVENTION

This invention relates to the catalytic cleavage of cumene hydroperoxide to equal molar portions of phenol and acetone in the presence of a halogen-substituted thiophenol catalyst.

DESCRIPTION OF THE PRIOR ART

Cumene can be readily oxidized with air to form cumene hydroperoxide and the hydroperoxide can then be decomposed to form equal molar amounts of phenol and acetone. In the commercial process for producing phenol by this general method, a small amount of a mineral acid, generally sulfuric acid, is used as the decomposition or cleavage catalyst. Since phenol and acetone are the products of the cleavage reaction, the reaction solvent can conveniently be a phenol-acetone solution. In this process the cumene hydroperoxide instantaneously decomposes to phenol and acetone as it is slowly added in solution with cumene to the mineral acid solution. The highly exothermic reaction is controlled by the rate of cumene hydroperoxide addition and by acetone reflux. Water is substantially excluded from the reaction medium during the decomposition reaction to insure homogeneity. These processing details are essentially described in U.S. Pat. No. 2,663,735.

DESCRIPTION OF THE INVENTION

The desired decomposition of cumene hydroperoxide is a cleavage to equal mols of phenol and acetone, that is, about 62 weight percent phenol and 38 weight percent acetone. In using sulfuric acid as the decomposition catalyst, a selectivity to phenol of about 85 to 95 percent is generally obtained. The non-selective decomposition product particularly as catalyzed by a strong mineral acid includes cumyl alcohol, acetophenone, methylbenzofuran, several organic acids, mono- and dicumylphenol, diacetone alcohol, acetol mesityl oxide, phorone, alphamethylstyrene and various oligomers of alpha-methylstyrene which are tar-like substances. When the reaction product is distilled, these by-products remain in the residue which is collectively called "tar" or "tars". It has been reported that the main products in this "tar" are cumylphenol and dicumylphenol, the polymers of alpha-methylstyrene, acetophenone and diacetone alcohol. Since few of these by-products of the non-selective reaction can be economically recovered, this non-selective reaction represents a significant economic loss.

A particular advantage of the halogen-substituted thiophenol catalysts of this invention in contrast with the strong mineral acid catalyst of the prior art is that there is essentially no tar formation with the halogen-substituted thiophenol because these catalysts do not promote the alkylation of phenol product to cumylphenol nor the oligomerization of aromatic olefin to form tars. A selectivity to phenol as high as 90 percent and higher is attainable in the present process with the major byproduct being alpha-methylstyrene, which can be recovered and hydrogenated to cumene for recycle in the process. A further advantage in the use of the halogen-substituted thiophenol catalysts instead of the mineral acid catalysts is that the corrosion problems of the latter are substantially avoided.

The catalyst of this invention is thiophenol having from one to five ring substituents selected from fluorine, chlorine and bromine. Included in this class of catalysts are p.fluorothiophenol; 2,4-dichlorothiophenol; 2,6-difluoro-4-chlorothiophenol; pentachlorothiophenol; pentafluorothiophenol; pentabromothiophenol and the like. The catalyst will readily dissolve in the reaction liquid. It can also be added as a solution in a solvent which is inert in the reaction such as acetone, benzene, cumene, toluene and the like.

We have found that the concentration of the catalyst is an important reaction variable. That is, the higher the catalyst concentration, the more rapid the reaction until too much catalyst renders the exothermic reaction uncontrollable. On the other hand, the reaction is too slow with too little catalyst. Some catalysts are active at lower concentrations, while other catalysts require higher amounts for a suitable rate of reaction. Within these constraints the concentration of the catalyst can be as low as about 20 parts per million parts of total reaction liquid (ppm.) up to about one percent, or even higher with appropriate control of reaction temperature, and preferably its concentration will be between about 500 ppm. and about 0.5 percent.

Since the cleavage reaction is highly exothermic, temperature control of the reaction liquid is generally provided. This temperature control can be accomplished by controlling the amount of catalyst used or by controlling the rate at which the catalyst is mixed with the cumene hydroperoxide. But with the highly active catalysts one or both of the following techniques for temperature control is desirably utilized. Temperature control can be effected, in part, by maintaining appropriate means for the positive cooling of the reaction liquid during the reaction such as by solvent reflux or by submerged cooling coils. Another effective and useful method of temperature control is the employment of sufficient inert solvent to serve as a heat sink. The reaction can be carried out within the range of between about 25° to about 110° C. and preferably a range of between about 60° to about 80° C. At the lower temperatures the reaction becomes quite slow although highly selective, while undesirable tar formation can result at higher temperatures due to the effects of thermal decomposition of the cumene hydroperoxide.

The pressure within the reactor is not a critical factor during the decomposition reaction. Generally, the pressure will range from a pressure moderately below to moderately above atmospheric pressure.

The cumene hydroperoxide can desirably be prepared by oxidation of cumene with air in the conventional manner. In this process a solution of at least about 10 weight percent cumene hydroperoxide in cumene is desirably produced, although a product containing less than 10 weight percent cumene hydroperoxide can be utilized. Since it is not particularly desirable to use an excessive amount of cumene in a continuous process as a reaction solvent due to subsequent handling and separation problems, it is preferred that a more concentrated solution of cumene hydroperoxide be prepared. In this oxidation reaction the maximum concentration of cumene hydroperoxide that can conveniently be produced is about 30 percent.

The cumene hydroperoxide to be used in the decomposition reaction can be further concentrated by flashing off sufficient cumene to form a feed solution of between about 60 to about 90 percent, preferably about 65 to about 80 percent, cumene hydroperoxide. Although pure cumene hydroperoxide can be used, it is not desirable to obtain it in this final stage of purity for economic reasons and also for safety reasons since the presence of some cumene tends to stabilize the cumene hydroperoxide. The decomposition reaction can suitably be carried out with as little as about 0.1 weight percent cumene hydroperoxide in the reaction liquid, with at least about 0.5 percent being preferred and at least about 1.0 percent being most preferred. The maximum amount of cumene hydroperoxide in the cleavage reaction liquid will suitably be about 20 weight percent, preferably about 10 percent and most preferably about 5 percent. Since explosions have in the past resulted from cumene hydroperoxide reactions which have run away, it is generally desired to carry out the reaction with substantial diluent as a safety measure, resulting in a concentration of cumene hydroperoxide in the reaction liquid much below the upper limit.

The solvent used in this process can be the cumene associated with the cumene hydroperoxide as described above. However, since phenol and acetone are the desired reaction product, a phenol-acetone solvent is generally desirable in order to simplify product separation. Since a solution of cumene hydroperoxide and cumene is usually added to the reactor, the solvent system will therefore include cumene as a component, generally a minor component. The solvent can conveniently be the 1:1 molar phenol to acetone product of the cumene hydroperoxide cleavage reaction, however, variations in the relative proportions can be used. Thus, although there is no particular advantage to using an excess of phenol, an excess of acetone may be desirable, particularly if the acetone is to be utilized for temperature maintenance during reaction by means of acetone reflux or boil-off. Therefore, the mol ratio of acetone to phenol as the solvent in the reaction mixture can be as high as about 10:1 and preferably no higher than about 3:1. Other usable solvents include aromatic solvents such as benzene, toluene, and the like; ethers such as diethyl ether and tetrahydrofuran, or any other solvent which is compatible with the reactant and catalyst and can be conveniently separated.

Phenol is not inert when used as a solvent for cumene hydroperoxide in its decomposition. Rather phenol, by virture of its acid nature, has been found to be a catalyst for the decomposition of cumene hydroperoxide in a reaction which is significantly slower than the above-described mineral acid catalyzed reaction. Moreover, the selectivity of this phenol catalyzed decomposition of cumene hydroperoxide is very poor, being less than 80 percent selectivity to phenol as determined by a study of the reaction. It is readily apparent that the presence of solvent phenol in the mineral acid catalyzed reaction of the commercial processes is not noticeably detrimental because the great speed of the mineral acid catalyzed decomposition effectively eliminates the detrimental effect on selectivity of the relatively slow phenol catalyzed reaction. In our reaction we can avoid a significant adverse effect on product selectivity from the phenol catalyzed reaction, particularly when phenol is present as an added solvent, by appropriate catalyst selection and/or concentration to obtain a suitably rapid reaction.

When operating under the general conditions described herein, particularly within a temperature range between about 60° and 80° C., the decomposition reaction to substantial completion, as a batch or as a continuous process, will take place in about two minutes to about two hours, and preferably will take place in about five to about 45 minutes. The process can also be carried out in a semi-continuous manner in which the reactant, solvent and catalyst are continuously added to a stirred tank reactor at a rate coinciding with the withdrawal rate, sufficient to provide a suitable average reaction rate within the above time ranges for substantially complete reaction. Since a significant quantity of unreacted cumene hydroperoxide in the final reaction product can undesirably interfere with the distillative separation procedure, it is preferred that there be a substantially complete decomposition of the cumene hydroperoxide in the reaction stage.

DESCRIPTION OF PREFERRED EMBODIMENTS

In the following examples, the hydroperoxide was analyzed by iodometric titration with sodium thiosulfate. The decomposition product resulting from the substituted thiophenol catalyzed reactions was light yellow in color and transparent, indicating very slight tar, while the sulfuric acid catalyzed product liquid was black and opaque. Both the residue and the product distillate were analyzed. The anlyses for compounds other than hydroperoxide were accomplished by gas chromatography or by high performance liquid chromatography.

EXAMPLE 1

The catalytic activity of sulfuric acid for the decomposition of cumene hydroperoxide was observed. A 57.3 percent solution of cumene hydroperoxide in cumene was added dropwise into 100 ml, of a two percent solution of sulfuric acid in acetone in a 300 ml. round bottom flask open to the atmosphere. Each drop instantly decomposed as it contacted the solution. Since no positive cooling of the reaction liquid was provided, the temperature of the solution rose from room temperature (about 25° C.) at the beginning of the addition to 44° C. upon the completion of the addition. A total of 35.2 g. of the cumene hydroperoxide was added over 60 minutes. Analysis of the product showed that 99.9 percent of the cumene hydroperoxide had reacted at a selectivity of 93 percent to phenol.

EXAMPLE 2

The following reactions were carried out in a glass reactor equipped with a magnetic stirrer and operated at a pressure within the reactor slightly above atmospheric pressure. The reactor was cooled by a cold finger in the liquid. Small samples of the reaction liquid (about 1 ml.) were periodically withdrawn to monitor the reaction.

Phenol was tested as a decomposition catalyst for cumene hydroperoxide at several temperatures. About 20 g. of a solution consisting of 5 parts phenol, 3 parts acetone and 1 part cumene were placed in the reactor. About 2 ml. of a solution consisting of 55 percent cumene hydroperoxide in cumene were injected into the reactor in each experiment. Table I summarizes the results of these experiments.

Table I

| Minutes | Cumene Hydroperoxide Decomposed, % | | | |
|---|---|---|---|---|
| | 10 | 20 | 50 | 100 |
| Temp | | | | |

Table I-continued

| Minutes | Cumene Hydroperoxide Decomposed, % | | | |
|---|---|---|---|---|
| | 10 | 20 | 50 | 100 |
| 40° C. | trace | trace | trace | trace |
| 60° C. | — | 8 | 19 | 39 |
| 80° C. | 18 | 34 | 60 | 85 |

The experiment at 80° C. was allowed to run for four and one-half hours at which time the cumene hydroperoxide was completely decomposed. Analysis of this product mixture disclosed that it contained 77 percent phenol, 8 percent alpha-methylstyrene, 4 percent acetophenone, 4 percent dimethylbenzyl alcohol, and 7 percent of a residuum consisting of aromatic carbonyls, aromatic alcohols, substituted phenols, substituted benzofurans and methylstyrene oligomers.

EXAMPLE 3

A 200 ml. glass reactor partially immersed in a heated oil bath at 60° C. and equipped with a magnetic stirrer and a cold finger was used in this experiment. The cold finger was cooled with tap water and was only used when necessary to prevent excessive temperatures. The reactor was charged with 22 g. of a 20 percent solution of cumene hydroperoxide (CHP) which heated to 60° C. After the cumene hydroperoxide solution had reached 60° C., 11 microliters (500 ppm.) of pentafluorothiophenol in 100 microliters of acetone were added to initiate the decomposition reaction. The temperature rose to 67° C. and the decomposition was completed in 15 minutes. Analysis of the reaction product showed 87 percent phenol, 8 percent alpha-methylstyrene, 3 percent acetophenone and 2 percent α,α-dimethylbenzyl alcohol.

EXAMPLE 4

Example 3 was repeated and the analysis of the reaction product showed 89 percent phenol, 8 percent alpha-methylstyrene and 3 percent acetophenone.

EXAMPLE 5

Another charge of 22 g. of 20 percent cumene hydroperoxide solution was placed in the reactor. The solution was heated to 80° C. and 250 ppm. of pentafluorothiophenol was injected in the reactor as a catalyst. The temperature rose to a maximum of 131° C. and substantially complete decomposition of the cumene hydroperoxide resulted. After 45 minutes, the product analysis showed a selectivity of 80 percent to phenol, 11 percent to alpha-methylstyrene, 7 percent to acetophenone and 2 percent to dimethylbenzyl alcohol.

EXAMPLE 6

The reactor was again charged with 22 g. of 20 percent cumene hydroperoxide solution. After heating the solution to 80° C., 15 microliters (680 ppm) of pentachlorothiophenol in 100 microliters of acetone were added. The temperature rose to 85° C. and in 25 minutes the cumene hydroperoxide was more than 99 percent decomposed. Analysis of the product showed a selectivity of 82 percent to phenol, 16 percent to alpha-methylstyrene and 2 percent to acetophenone.

When this experiment is repeated using pentabromothiophenol, similar results are obtained.

EXAMPLE 7

Another charge of 22 g. of 20 percent cumene hydroperoxide was heated to 80° C. in the reactor and 5 microliters (242 ppm.) of thiophenol in 100 microliters of acetone was charged to the reactor. The temperature rose to 86° C. during the decomposition of the cumene hydroperoxide. Analysis of the product mixture after 30 minutes at the reaction temperature showed a selectivity of 65 percent phenol, 30 percent alpha-methylstyrene, 4 percent acetophenone and one percent dimethylbenzyl alcohol.

EXAMPLE 8

An additional charge of 22 g. of 20 percent cumene hydroperoxide was placed in the reactor and heated to 60° C. and 0.02 gram of pentafluorophenol was charged into the reactor. The temperature rose to 68° C. and in 15 minutes the decomposition was substantially complete. Product analyses showed a selectivity to phenol of 71 percent, to alpha-methylstyrene 21 percent, to acetophenone 7 percent and to dimethylbenzyl alcohol one percent.

It is to be understood that the above disclosure is by way of example and that numerous modifications and variations are available to those of ordinary skill in the art without departing from the true spirit and scope of the invention.

We claim:

1. The method for cleaving cumene hydroperoxide at high selectivity to phenol and acetone which comprises contacting a solution comprising about 0.1 to about 20 weight percent cumene hydroperoxide with a catalytic amount of thiophenol having from one to five ring substituents selected from fluorine, chlorine, bromine and mixtures thereof at a temperature between about 25° and about 110° C.

2. The method for cleaving cumene hydroperoxide at high selectivity to phenol and acetone in accordance with claim 1 in which the catalyst is present in an amount between about 20 ppm. and about one weight percent.

3. The method for cleaving cumene hydroperoxide at high selectivity to phenol and acetone in accordance with claim 1 in which the solution comprises between about one and about five weight percent cumene hydroperoxide.

4. The method for cleaving cumene hydroperoxide at high selectivity to phenol and acetone in accordance with claim 1 in which the solution comprises phenol and acetone in a mol ratio between about 1:1 and about 1:10.

5. The method for cleaving cumene hydroperoxide at high selectivity to phenol and acetone in accordance with claim 1 in which the temperature is maintained between about 60° and about 80° C. by reflux of the acetone.

6. The method for cleaving cumene hydroperoxide at high selectivity to phenol and acetone in accordance with claim 1 in which there is between about 500 ppm. and about 0.5 weight percent of the catalyst.

7. The method for cleaving cumene hydroperoxide at high selectivity to phenol and acetone in accordance with claims 2 or 6 in which the catalyst is pentachlorothiophenol.

8. The method for cleaving cumene hydroperoxide at high selectivity to phenol and acetone in accordance with claims 2 or 6 in which the catalyst is pentafluorothiophenol.

* * * * *